United States Patent [19]

Case

[11] 4,448,883

[45] May 15, 1984

[54] METHOD OF MAKING LYOPHILIZED TERMINAL DEOXYNUCLEOTIDYL TRANSFERASE

[75] Inventor: Richard V. Case, Midland, Tex.

[73] Assignee: The Midland Certified Reagent Company, Midland, Tex.

[21] Appl. No.: 401,812

[22] Filed: Jul. 26, 1982

[51] Int. Cl.³ ........................... C12N 9/12; C12N 9/96
[52] U.S. Cl. ..................................... 435/194; 435/188
[58] Field of Search ................ 435/193, 183, 188, 194

[56] References Cited

U.S. PATENT DOCUMENTS 4,339,533  7/1982  Chu .................................. 435/188 X
4,342,827  8/1982  Atkinson et al. ................ 435/188 X

OTHER PUBLICATIONS

Methods in Enzymology vol. XXII, pp. 32–38 (1971).

*Primary Examiner*—Lionel M. Shapiro
*Attorney, Agent, or Firm*—Oblon, Fisher, Spivak, McClelland & Maier

[57] ABSTRACT

Heat sensitive terminal deoxynucleotidyl transferase is stabilized by lyophilizing a solution of the enzyme, said solution prior to freeze-drying having a carefully controlled pH, an ionic concentration of at least 0.05 mole/liter and a protein concentration of greater than 0.3 gram/liter.

7 Claims, No Drawings

METHOD OF MAKING LYOPHILIZED TERMINAL DEOXYNUCLEOTIDYL TRANSFERASE

BACKGROUND OF THE INVENTION

1. Field of the Invention

This invention relates to a process for preparing a thermally stable, readily transportable, lyophilized enzyme, terminal deoxynucleotidyl transferase (TDT), and the freeze-dried enzyme resulting therefrom.

2. Description of the Prior Art

An enzyme is a protein with catalytic properties due to its power of specific activation. The characteristic property of enzymes is their power of catalyzing certain definite chemical reactions in aqueous media. To study enzymes, as well as to use them in many applications, it is necessary to remove them from their natural environment and isolate them for use or storage. Under unsuitable conditions, these materials undergo conformational changes, denaturation and inactivation. In removing them from their natural environment, and in their subsequent handling, the first consideration must always be to avoid inactivation.

Success in dealing with enzymes depends upon avoiding conditions under which they are unstable, and, while conditions vary with the particular enzyme in question, in general, high temperature environments are especially to be avoided with all enzyme materials, with many enzyme treatments carried out at or near 0° C. as a matter of course.

In most cases, there is inactivation of enzymes on standing, even under the most favorable conditions, and the storing of enzymes without loss of activity is a significant problem. When an enzyme solution can be frozen and thawed without loss of activity, it is sometimes most convenient to keep it in the frozen state at a temperature of about −20° C., in which state it may be stored stably for from a few weeks to several months. However, this method entails special handling and equipment, and the transportation of these frozen enzymes creates similar problems in handling and equipment. Drying of enzymes is another method which has been used, but problems occur here also, and the shelf-life stability of the dried enzyme is not uniform.

Terminal deoxynucleotidyl transferase (TDT) was first discovered over twenty years ago and purified to homogeneity from animal thymus glands in 1971. Like other DNA polymerases, it forms or extends the length of polydeoxynucleotide, requires low concentrations of magnesium or other divalent metal ions as cofactor, and utilizes the deoxynucleotide-5'-triphosphates as substrate. The unique feature of TDT is that, unlike other DNA polymerases, it does not require a template, i.e., a first strand of DNA to be copied in forming the classical double-stranded helix. Rather, TDT extends a "primer," which must be at least three deoxynucleotide residues in length, using whatever deoxynucleotide-5'-triphosphate is available. The product formed is typically single-stranded DNA. TDT is now widely used in genetic engineering and in the synthesis of certain unique types of DNA polymers.

TDT has been commercially available since about 1971. The commercially available form of TDT has always been a buffered, aqueous 50% glycerol solution of the highly purified enzyme, the glycerol acting as a stabilizing agent and bacteriostat for the enzyme. Other methods of stabilizing the enzyme, including freezing and freeze-drying, have reportedly been unsuccessful.

The increase in the use of TDT for various types of biochemical research has resulted in an increase in the need for a storage-stable, easily transportable TDT enzyme product. Unfortunately, prior to the present invention, the commercially available products have suffered from the disadvantage that they possess very poor thermal stability, thus requiring carefully modulated thermal control during shipping and storing in order to maintain a substantial degree of enzymatic activity.

While *Methods in Enzymology*, Volume XXII, Pages 32–38, 1971 and Neubeck, U.S. Pat. No. 4,180,917, suggest that lyophilization of enzymes requires removal of all ions by dialysis prior to lyophilization, removal of all ions from solutions of TDT results in protein aggregation, precipitation of the enzyme, and subsequent loss of essentially all enzymatic activity.

Therefore, a need has continued to exist for terminal deoxynucleotidyl transferase of high thermal stability, capable of being maintained in storage or shipping at ambient temperatures, which, upon reconstitution, still maintains substantially all of its biocatalytic activity.

SUMMARY OF THE INVENTION

It is, therefore, an object of this invention to prepare terminal deoxynucleotidyl transferase of high thermal stability.

It is another object of this invention to prepare terminal deoxynucleotidyl transferase which may be kept at ambient temperature for longer periods than heretofore possible without any appreciable loss in biocatalytic activity.

It is another object of this invention to prepare terminal deoxynucleotidyl transferase which may be transported at ambient temperatures without any appreciable loss in biocatalytic activity.

It is yet a further object of this invention to prepare thermally stable TDT in dried form, which, upon reconstitution, maintains substantially all of its biocatalytic activity.

These and other objects of the invention, as will hereinafter become more readily apparent, have been accomplished by lyophilizing a buffered solution of terminal deoxynucleotidyl transferase, said solution prior to lyophilizing having a carefully controlled pH, an ionic concentration of at least 0.05 moles/liter, and a protein concentration of greater than 0.3 gram/liter, thereby producing a lyophilized terminal deoxynucleotidyl transferase.

DESCRIPTION OF THE PREFERRED EMBODIMENT

The recovery and purification of terminal deoxynucleotidyl transferase is disclosed by Lucy Chang and Frederick Bollum, *Journal of Biological Chemistry*, Volume 246, No. 4, Pages 909–916, Feb. 25, 1971. However, efforts to lyophilize the enzyme solutions thus prepared do not yield a satisfactory result.

The critical difference between the Chang and Bollum enzyme recovery and the enzyme recovery of this invention lies in the final pH of the enzyme solution. While Chang and Bollum require a final pH of 4.5, this invention requires that the pH of the solution prior to lyophilization be in the range of 6.0 to 10 (with 7.0 to 8.5 the preferred pH range), the pH range of Chang and Bollum not permitting a quantitative recovery of enzyme activity in the reconstituted enzyme.

As is readily apparent from the above, the recovery and purification of terminal deoxynucleotidyl transferase necessarily involves the addition of phosphate ion to the protein containing solution. Previous attempts at lyophilizing terminal deoxynucleotidyl transferase have not been successful. It has now been discovered that these solutions can be lyophilized if certain conditions are met.

Terminal deoxynucleotidyl transferase is obtained by suspending ground thymus in a buffered salt solution. Suitable buffers are well-known to the art and include those which will effectively control the pH within the desired range of 6.0 to 10.0. The preferred buffer is $K-PO_4$. In this and other instances throughout, $K-PO_4$ should be understood to mean that mixture of monobasic and dibasic potassium phosphates which gives the stated pH in the solution. Suitable salts useful for extracting the enzyme from the suspension of ground thymus include the alkali metal chlorides, with the preferred salt being NaCl. Typically, the thymus is suspended in two to six times its weight of the buffered salt solution and stirred intermittently for one to twenty hours, the concentration of the salt solution being in the range of 0.01 mole/liter to 0.09 mole/liter, with 0.04 mole/liter being a preferred concentration. Typical concentrations of the buffering agent are in the range of 0.005 to 0.10 mole/liter, depending on the buffering agent employed.

It is a common practice, and well-known in the art, to include a stabilizer in this initial extraction step. From among the numerous well-known stabilizers, ethylene diaminetetraacetic acid (EDTA) is preferred, in an amount sufficient to provide the necessary stabilization, typically in a concentration of 0.0005 to 0.005 mole/liter.

The solution is separated from the solid material, typically by settling and decantation followed by adsorption to a suitable ion-exchange material. Typical and preferred as the ion-exchanger is phosphocellulose. Following separation of the ion-exchanger with adsorbed enzyme from the solution, the TDT is further purified. A preferred method of purification involves introduction into a chromatographic column followed by elution with a buffered solution of water having a pH within the range described above. A protein peak emerges, said protein peak containing essentially all of the TDT.

A subsequent purification for removal of residual nucleic acids is effected. The preferred method for removal of these nucleic acids involves passing the solution through another ion exchanger, with the preferred method involving the use of a DEAE cellulose anion exchanger.

The TDT is now collected and concentrated, a typical procedure for same involving precipitation, the precipitation typically effected with $(NH_4)_2SO_4$ at 70% saturation, followed by separation by filtration or centrifugation, with centrifugation being the preferred method of separation.

The precipitated enzyme is now redissolved in a buffered salt solution in preparation for additional purification.

According to the practice of this invention, the enzyme solution from the redissolving of the precipitated enzyme is now treated in such a manner as to effect further purification, while maintaining the ion concentration, enzyme concentration, and pH within carefully controlled limits.

Surprisingly, it has now been found that the ion concentration of the enzyme-containing solution is extremely critical for obtaining a lyophilized product having satisfactory enzymatic activity, and it is this discovery which makes up another essential aspect of the claimed invention. If the ion concentration is allowed to drop below 0.05 moles/liter, the resulting lyophilized enzyme product has essentially no enzymatic activity. The preferred salt with which this concentration is obtained is potassium chloride. However, this invention is not limited to the use of potassium chloride but includes other metal halides and organic hydrohalides, and other salts that are essentially free of inhibitory influence upon the catalytic activity of the reconstituted enzyme.

Other salts which have proved satisfactory are tris-hydroxymethyl-aminomethane hydrochloride, potassium phosphate and triethylammonium-bicarbonate, the latter having the added advantage of subliming during lyophilization to yield a product free from simple ions in the freeze-dried state, but yielding, upon reconstitution with aqueous solutions of suitable ionic strength, a solution having satisfactory enzyme activity. These salts have the added advantage of serving as buffers for the enzyme solutions.

The enzyme-containing solution prior to lyophilization may also contain glycerol, although it is not necessary that the glycerol be present. When present the glycerol occurs in amounts ranging from 0.05% to 0.70% by volume of the solution prior to lyophilization.

Another essential aspect of the instant invention is the discovery of the extreme importance of protein concentration in obtaining a lyophilized enzyme having substantial biocatalytic activity upon reconstitution. Enzyme concentrations of less than 0.3 grams of protein per liter result in a lyophilized product having essentially no biocatalytic activity upon reconstitution. While a concentration level of 1 gram/liter appears to be optimal, satisfactory results are obtained over a concentration range of 0.3 grams/liter to as high as 4 grams/liter and above.

Typically, the redissolved enzyme solution, appropriately buffered in a solution containing sufficient ionic strength within the limits set out above and having an enzyme concentration within the requirements as set out above, is further purified by methodology which permits the above conditions to be met. Typically, the solution containing TDT can be dialyzed against a solution with the desired pH and ionic make-up followed by a molecular weight fractionation by gel filtration chromatography, the fraction falling within 18,000 and 2 million containing the TDT activity. This solution can be lyophilized at this point or can be further purified by subsequent steps directed to a more homogenous product, such steps including affinity chromatography, hydroxylapatite chromatography, and rechromatography on phosphocellulose.

Lyophilization is carried out using conventional techniques and equipment. Temperature ranges of $-60°$ C. (frozen solution of TDT) to $+40°$ C. (substantially dry product) are within the contemplation of this invention, with the preferred temperature range being approximately $-40°$ C. to $+20°$ C. Pressures of 0.1 to 200 milliTorr are in the preferred pressure range.

Terminal deoxynucleotidyl transferase is an extremely important biocatalytic material in genetic engineering. It is used to extend the 3' end of double stranded DNA prior to annealing same with another DNA in order to produce a chimera. Additionally, this enzyme is used in the synthesis of specific polydeoxynucleotides and is essential and is the only known catalyst for the synthesis of homopolydeoxynucleotides. Additional uses of the enzyme are in the radioactive labeling of the terminal or the terminus of a DNA molecule and in the sequence analysis of DNA.

Having now generally described this invention, the same will be better understood by reference to certain specific examples, which are included herein for purposes of illustration only and are not intended to be limiting of the invention or any embodiment thereof, unless specified.

EXAMPLE 1

Separation and Purification of TDT

Thymus gland obtained from a packing house is ground while frozen, mixed with four times its weight of a buffer solution of 0.04 mole/liter K-PO$_4$, 0.04 mole/liter NaCl, 1 mg/liter pepstatin A (a protease ihibitor), 1 mmole/liter ethylenediaminetetraacetic acid (EDTA), and 1 mmole/liter 2-mercaptoethanol pH 7.0 to 7.4, 2-mercaptoethanol used as a reducing agent to keep the enzyme in its reduced stage. This and subsequent purification steps are performed at 4° C. The solution containing thymus glands is stirred intermittently for two hours and then permitted to settle for one hour. A crude fraction is obtained by decantation and filtration through glass wool. This crude fraction is left to stand overnight and then decanted again to remove additional sediment which has accumulated in the settling process. This crude extract is adsorbed on 1 kilogram of phosphocellulose which has been precycled and equilibrated with 0.05 mole/liter K-PO$_4$, 1 mmole/liter EDTA, and 1 mmole/liter 2-mercaptoethanol, the pH of which is 7.0. The supernatant liquid is decanted and the phosphocellulose containing the adsorbed protein is washed by suspension and decantation in 0.05 mole/liter K-PO$_4$, again at pH 7.0. The enzyme-containing suspension is then transferred to a chromatographic column and eluted successively with 12 liters of 0.1 mole/liter K-PO$_4$ and then 20 liters of 0.4 mole/liter K-PO$_4$ having a pH of 7.2. A protein peak emerges and the terminal deoxynucleotidyl transferase is found therein. The active enzyme fractions are then pooled and passed through DEAE-cellulose anion exchanger, removing other residual nucleic acids. The protein eluate is combined and precipitated with amonium sulfate (NH$_4$)$_2$SO$_4$ at 70% of saturation, and the precipitated protein separated from the solution by centrifugation. The precipitated protein is now redissolved in 0.05 mole/liter K-PO$_4$, pH 7.0. This soluttion is dialyzed overnight and fractionated with ammonium sulfate (NH$_4$)$_2$SO$_4$, the fraction between 35% and 55% ammonium sulfate being collected by centrifugation. This precipitate is now resuspended at maximum protein concentration in 0.05 mole/liter K-PO$_4$ containing 1 mmole/liter EDTA, 1 mmole/liter 2-mercaptoethanol at a pH of 7.0, and also containing from 0.05 to 0.5 mole/liter potassium chloride. The resuspended enzyme solution is now fractionated on Sephadex®G-100, which performs a separation based on molecular weight, using chromatographic markers which permit recovery of the molecular weight fraction falling between 18,800 and 2 million. Sephadex® is a registered trademark of Pharmacia Fine Chemicals, Inc. This fraction is routinely screened for nuclease by incubating with polydeoxynucleotides.

EXAMPLE 2

Enzyme purified according to Example 1 was dialyzed against 3 changes of each of the following solutions:
A. Deionized water
B. 2 mmole/liter potassium cacodylate containing 0.1 mmole/liter MgCl$_2$, pH 7
C. 2 mmole/liter potassium cacodylate containing 0.1 mmole/liter EDTA, pH 7
D. Deionized water containing 0.1% v/v glycerol The protein concentration of the solution prior to dialysis was 3.6 grams/liter. Protein precipitation occurred upon dialysis against all 4 solutions. The precipitate was removed, and aliquots of the dialyzed enzyme were lyophilized. Thereafter, the lyophilized materials were reconstituted to their original volume by the addition of deionized water and assayed for TDT activity.

| Enzyme Dialyzed Against Solution | Enzyme Assayed | Relative Activity (CPM) |
|---|---|---|
| A. | Dialyzed only, not lyophilized | 115 |
| A. | Dialyzed and lyophilized | 23 |
| B. | Dialyzed only, not lyophilized | 26 |
| B. | Dialyzed and lyophilized | 21 |
| C. | Dialyzed only, not lyophilized | 24 |
| C. | Dialyzed and lyophilized | 23 |
| D. | Dialyzed only, not lyophilized | 200 |
| D. | Dialyzed and lyophilized | 292 |
| none | Control enzyme, not dialyzed | 697 |
| none | Control enzyme, not dialyzed | 725 |

In this and all subsequent examples where activity is given as CPM, no correction for background radiation has been made; background radiation typically contributes approximately 20 CPM to the observed count rate under the conditions used.

The enzyme assay in this and the subsequent Examples was performed according to the method set out in Bollum and Chang, Supra. Activity is measured in counts per minute (CPM), or in the international units per liter (IU/L).

As can be seen from the results of this Example, where the enzyme solution ion concentration was not maintained at a sufficient level, significant loss of enzyme activity resulted.

EXAMPLE 3

The enzyme preparations of Example 2, A (dialyzed against deionized water) and D (dialyzed against deionized water containing 0.1% v/v glycerol) were supplemented with various substances to determine if any could preserve enzyme activity during freeze-drying. The supplements, at the final concentrations given in the table, were added to the enzyme preparations just prior to lyophilization. After lyophilization, each sample was reconstituted to its original volume with deionized water and assayed for TDT activity.

| Experiment Number | Enzyme Preparation of Example 2 | Supplement | Relative Activity (CPM) |
|---|---|---|---|
| 1 | D | none | 89 |
| 2 | A | 0.1% glycerol | 73 |

-continued

| Experiment Number | Enzyme Preparation of Example 2 | Supplement | Relative Activity (CPM) |
|---|---|---|---|
| 3 | D | 0.045 mole/liter K phosphate, 1.8 mmoles/liter $MgCl_2$, pH 7 | 63 |
| 4 | A | 0.045 mole/liter K phosphate, 1.8 mmoles/liter $MgCl_2$, pH 7 | 35 |
| 5 | D | 0.045 mole/liter K phosphate, pH 7 | 38 |
| 6 | A | 0.045 mole/liter K phosphate, pH 7 | 34 |
| 7 | D | 0.045 mole/liter Tris-HCl, pH 8.2 | 27 |
| 8 | A | 0.045 mole/liter Tris-HCl, pH 8.2 | 54 |
| 9 | D | 0.045 mole/liter HEPES, pH 7.3 | 48 |
| 10 | A | 0.045 mole/liter HEPES, pH 7.3 | 41 |
| 11 | D | dialyzed but not lyophilized | 117 |
| 12 | A | dialyzed but not lyophilized | 135 |

Thus it may be seen that conventional buffering supplements were either detrimental to or offered no advantage to the addition of 0.1% glycerol alone.

EXAMPLE 4

Enzyme purified as in Example 1 was dialyzed against 0.05 moles/liter K-$PO_4$, 2 mmoles/liter $MgCl_2$, 1 mmole/liter 2-mercaptoethanol, and 0.1% v/v glycerol, pH 7. The protein concentration was 0.98 grams/liter. The dialyzed enzyme solution was supplemented with additional glycerol to give the final concentration shown in the table. These preparations were then lyophilized, reconstituted to their original volume, and assayed for TDT activity.

| Final concentration of glycerol (prior to lyophilization) | turbidity upon reconstitution? | Relative Activity (CPM) |
|---|---|---|
| 0.1% | no | 456 |
| 0.3% | no | 442 |
| 0.5% | no | 360 |
| 0.9% | no | 28 |
| 1.5% | yes | 24 |
| 2.1% | yes | 18 |
| Control, dialyzed but not lyophilized | | 573 |

The difference between this Example and the previous one is that in Example 3 the enzyme was dialyzed against deionized water, then supplemented with phosphate buffer, whereas in the present Example, dialysis was against phosphate buffer solution only.

Comparing the 0.1% glycerol-containing sample of this Example with Example 2, experiment number 3, it is to be noted that addition of ion following dialysis was not sufficient to provide a satisfactory result.

EXAMPLE 5

TDT purified as set out in example 1, with protein concentration 3.9 grams/liter, was dialyzed against one of the solutions below:

| Experiment Number | Solution Used for Dialysis |
|---|---|
| 1 | 0.1 moles/liter triethylammonium bicarbonate, pH 8.4, containing 0.1% v/v glycerol (solution A) |
| 2 | 0.02 moles/liter triethylammonium bicarbonate, pH 8.4, containing 0.1% v/v glycerol (solution B) |
| 3 | 0.1 moles/liter KCl, without any buffer, containing 0.1% v/v glycerol (solution C) |

After 13 hours of dialysis, a voluminous precipitate, presumed to be denatured protein, was present in the enzyme of experiment 2. A slight precipitate was present in experiment 3. Dialysis against a second change of solution was performed, with the concentration of buffer being increased to 0.05 moles/liter triethylammonium bicarbonate in the case of experiment 2. After the second dialysis, aliquots of the enzyme were lyophilized and then reconstituted to their original volume. They were then assayed for TDT activity.

| Enzyme of Experiment | Activity | % of Control |
|---|---|---|
| Control, not lyophilized | 180 IU/L | taken as 100% |
| #1 above | 145 IU/L | 80% |
| #2 above | 107 IU/L | 59% |
| #3 above | 145 IU/L | 80% |

This Example shows that *no* buffer at all needs to be present during the lyophilization, and that a volatile buffer (triethylammonium bicarbonate sublimes during the lyophilization process) may be used to maintain ionic strength prior to lyophilization.

It is to be noted that, where the ionic strength of the solution is not maintained above a certain critical level, enzyme activity is not recoverable.

EXAMPLE 6

TDT purified as in Example 1 was dialyzed against 0.2 mole/liter KCl, 0.02 mole/liter tris-HCl, pH 7.6, and an attempt was made to lyophilize this material at a protein concentration of 0.3 gram/liter. Only 17% of the activity was recovered.

Another portion of the highly purified enzyme was concentrated by precipitation with 90% saturated ammonium sulfate and then dialyzed against the same buffer as above. After the treatment, the protein concentration was 2.84 gram/liter. Portions of this solution were diluted with additional buffer prior to lyophilization, then reconstituted to the original volume for TDT assay.

| Enzyme preparation | Protein concentration (g/L) | Activity (IU/L) |
|---|---|---|
| Control, dialyzed but not lyophilized | 2.84 | 756 |
| Lyophilized | 2.84 | 651 |
| Lyophilized | 1.42 | 559 |
| Lyophilized | 0.95 | 486 |
| Lyophilized | 0.71 | 360 |
| Lyophilized | 0.57 | 435 |

These results show the dependence of enzyme activity recovery upon protein concentration at the time of lyophilization.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method of stabilizing the bio-catalytic activity of heat-sensitive terminal deoxynucleotidyl transferase (TDT) comprising lyophilizing a solution of the enzyme, said solution prior to lyophilization having a pH in the range of 6.0 to 10.0, an ionic concentration of at least 0.05 mole/liter and a protein concentration of 0.3 gram/liter or greater, comprising the steps of:
   (a) maintaining the pH of the solution at 6.0–10.0;
   (b) maintaining the ionic concentration of the solution at a concentration of the solution at a concentration of 0.05 mole/liter or above;
   (c) maintaining the protein concentration above 0.3 gram/liter; and
   (d) lyophilizing said solution, whereby a lyophilized terminal deoxynucleotidyl transferase having substantial biocatalytic activity is obtained.

2. The method of claim 1 comprising the steps of:
   (a) maintaining the pH in a range of 6.0–10.0;
   (b) maintaining the ionic concentration of the solution at a concentration of at least 0.2 mole/liter;
   (c) stabilizing the solution by addition of an effective amount of a stabilizing agent;
   (d) maintaining the protein concentration at 0.3 gram/liter or greater; and
   (e) lyophilizing said solution whereby a freeze-dried terminal deoxynucleotidyl transferase having substantial biocatalycic activity is obtained.

3. The method of claim 1 wherein the ionic concentration is maintained by salts selected from the group consisting of KCl, tris-hydroxymethylaminomethane and its hydrochloride, potassium phosphate, and triethylammonium bicarbonate or combinations of these.

4. The method of claim 2 wherein the pH of the buffered solution is from 7.0 to 8.5.

5. The method of claim 2 wherein the stabilizing agent is glycerol.

6. The method of claim 5 wherein the glycerol concentration is 0.05 to 0.70% by volume of the solution prior to lyophilization.

7. The method of claim 1 wherein lyophilization is achieved over a temperature range of $-60°$ C. to $+40°$ C. and pressures of 0.1 to 200 milliTorr.

* * * * *